(12) United States Patent
Seyler

(10) Patent No.: US 10,195,093 B2
(45) Date of Patent: Feb. 5, 2019

(54) ABSORBENT ARTICLE WITH THREE-DIMENSIONAL FILM FOR LIQUID DISTRIBUTION

(71) Applicant: TREDEGAR FILM PRODUCTS CORPORATION, Richmond, VA (US)

(72) Inventor: Rickey J. Seyler, Chesterfield, VA (US)

(73) Assignee: TREDEGAR FILM PRODUCTS CORPORATION, Richmond, VA (US)

( * ) Notice: Subject to any disclaimer, the term of this patent is extended or adjusted under 35 U.S.C. 154(b) by 425 days.

(21) Appl. No.: 14/918,085

(22) Filed: Oct. 20, 2015

(65) Prior Publication Data

US 2016/0106602 A1    Apr. 21, 2016

Related U.S. Application Data

(60) Provisional application No. 62/066,210, filed on Oct. 20, 2014.

(51) Int. Cl.
| | |
|---|---|
| *A61F 13/15* | (2006.01) |
| *A61F 13/20* | (2006.01) |
| *A61F 13/515* | (2006.01) |
| *A61F 13/512* | (2006.01) |
| *A61F 13/537* | (2006.01) |
| *A61F 13/511* | (2006.01) |
| *A61F 13/51* | (2006.01) |

(52) U.S. Cl.
CPC .......... *A61F 13/515* (2013.01); *A61F 13/512* (2013.01); *A61F 13/5123* (2013.01); *A61F 13/51121* (2013.01); *A61F 13/537* (2013.01); *A61F 13/53713* (2013.01); *A61F 13/53717* (2013.01); *A61F 2013/51014* (2013.01); *A61F 2013/51023* (2013.01); *A61F 2013/51078* (2013.01); *A61F 2013/51092* (2013.01)

(58) Field of Classification Search
CPC .................. A61F 13/512; A61F 13/537; A61F 13/53713; A61F 2013/51014
See application file for complete search history.

(56) References Cited

U.S. PATENT DOCUMENTS

| | | | |
|---|---|---|---|
| 4,342,314 A | 8/1982 | Radel et al. | |
| 4,395,215 A | 7/1983 | Bishop | |
| H001377 H * | 11/1994 | Perry | A61F 13/15 604/385.24 |
| 5,603,707 A | 2/1997 | Trombetta et al. | |
| 2002/0177826 A1 * | 11/2002 | Davis | A61B 46/40 604/358 |
| 2002/0187322 A1 * | 12/2002 | Molee | A61F 13/15203 428/212 |
| 2005/0261649 A1 * | 11/2005 | Cohen | A61F 13/53747 604/383 |
| 2005/0267429 A1 * | 12/2005 | Cohen | A61F 13/53747 604/378 |
| 2009/0299316 A1 | 12/2009 | Seyler | |

(Continued)

FOREIGN PATENT DOCUMENTS

WO    WO 1996/039109 A1    12/1996

*Primary Examiner* — Michele M Kidwell
(74) *Attorney, Agent, or Firm* — Karceski IP Law, PLLC

(57) ABSTRACT

An absorbent article with a three-dimensional film transfer layer having an open lattice structure formed from a single film for improved user properties.

19 Claims, 4 Drawing Sheets

(56) References Cited

U.S. PATENT DOCUMENTS

| | | | |
|---|---|---|---|
| 2011/0183109 A1* | 7/2011 | Seyler | A61F 13/53713 428/132 |
| 2011/0196330 A1* | 8/2011 | Hammons | A61F 13/512 604/383 |
| 2011/0293886 A1* | 12/2011 | Maschino | C08J 5/18 428/138 |
| 2012/0310197 A1* | 12/2012 | Thomas | A61F 13/53713 604/378 |
| 2017/0105887 A1* | 4/2017 | Thomas | A61F 13/513 |
| 2017/0165880 A1* | 6/2017 | Thomas | B29C 41/26 |

* cited by examiner

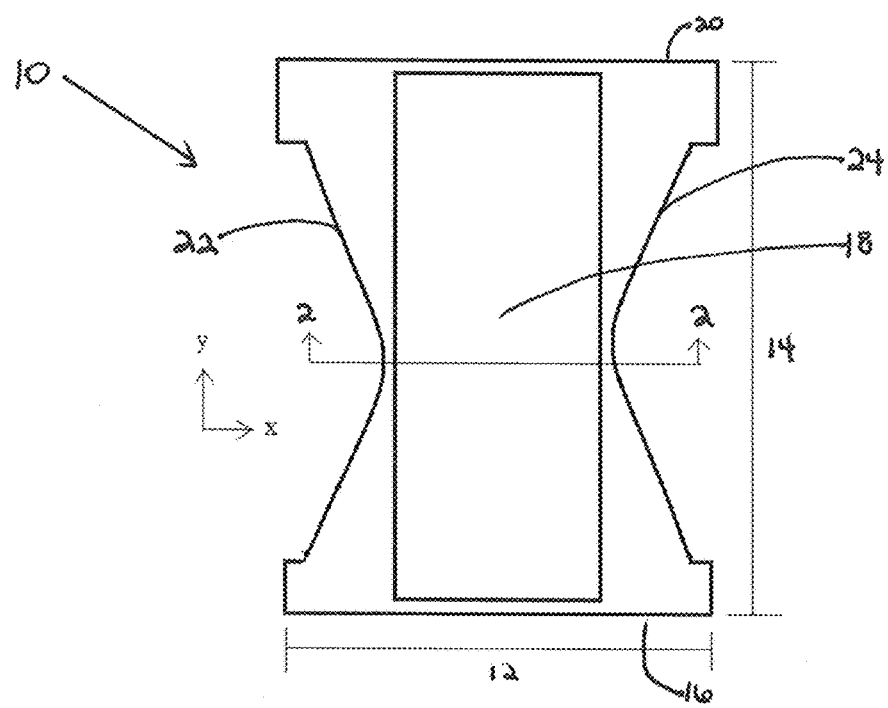
Figure 1
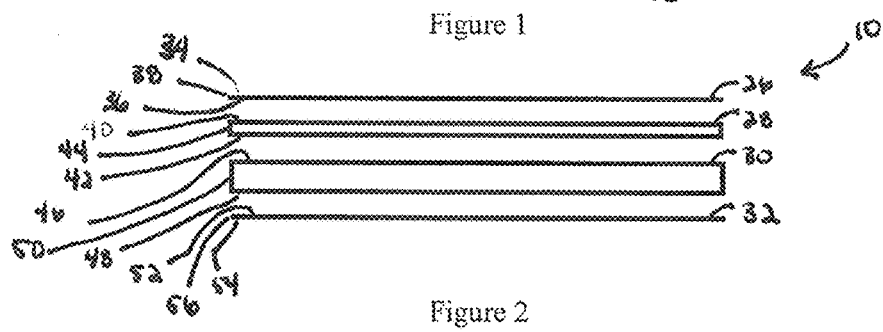
Figure 2
Figure 3

ABSORBENT ARTICLE WITH THREE-DIMENSIONAL FILM FOR LIQUID DISTRIBUTION

CROSS-REFERENCE TO RELATED APPLICATIONS

This application claims the benefit of U.S. Provisional Application No. 62/066,210, filed Oct. 20, 2014, the disclosure of which are incorporated herein by references in their entirety.

TECHNICAL FIELD

Examples herein relate to an absorbent article comprising a three-dimensional film for liquid distribution providing an end user experience of comfort and performance of handling insults in an absorbent article.

BACKGROUND

A transfer layer, which is also known in the art as an acquisition distribution layer or "ADL", has been used in absorbent articles to improve comfort by reducing rewetting or evacuation of the bodily fluids contained in the absorbent core to the users' skin. A transfer layer is typically positioned between the topsheet and the absorbent core of an absorbent article. Transfer layers have been employed to promote lateral flow of fluids in a direction generally parallel to the plane of the transfer layer, thereby permitting more surface area of the absorbent core to be used to absorb the bodily fluids. These types of transfer layers may be alternatives to nonwoven materials to provide improved protection against rewetting (evacuation of insults from the core of the absorbent article back through the topsheet) and to improve distribution of insults to the absorbent core. However, some users perceive, for example, actually or visually that the transfer layers may result in increased stiffness or discomfort to the user and therefore prefer seeing a nonwoven material in combination with the topsheet of the absorbent article. As such, a resilient plastic web exhibiting a fiber-like appearance may be provided in current examples. Unfortunately, users tend to find the fibers in such current plastic webs to be too defined and perceive the resilient plastic web to be more rigid than desired, and, thus, do not provide a balance in user perceived comfort and performance in handling insults in an absorbent article.

SUMMARY

An absorbent article may be provided. The absorbent article may include a topsheet material having a first surface, a second surface and thickness there between; a three dimensional film having a top plane, a thickness, a bottom plane, a width, a length and a loft, the loft comprising an open lattice structure comprising a random series of interconnected film fibers comprising a plurality of upper peaks and a plurality of lower peaks and a plurality of irregularly shaped apertures formed from the random series of interconnected film fibers, the interconnected film fibers being formed from the thickness of the film; an absorbent core comprising a first surface, a second surface, a thickness between the first and second surfaces, a width and a length; and a backsheet comprising a first surface, a second surface, a thickness between the first and second surfaces. In an example, the topsheet material second surface such as a bottom layer or surface thereof and the three-dimensional film top plane are in contiguous contact, the three-dimensional film bottom plane and the absorbent core first surface such as top layer or surface thereof are in contiguous contact, the absorbent core second surface and the backsheet first surface such as a top layer or surface thereof are in contiguous contact, the topsheet material second surface and the backsheet first surface encompass the three-dimensional film width and length and the absorbent core width and length. Additionally, in the three-dimensional film, the top plane may be formed from upper peaks of the random series of interconnected film fibers and the bottom plan is formed from the lower peaks of the random series of interconnected film fibers and the three-dimensional film loft and the lower peaks of the random series of interconnected film fibers comprise the irregularly shaped apertures.

The Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to any limitations that solve any or all disadvantages noted in any part of this disclosure.

BRIEF DESCRIPTION OF THE DRAWINGS

A more detailed understanding of the embodiments disclosed herein may be had from the following description, given by way of example in conjunction with the accompanying drawings.

FIG. 1 depicts a top plane view of an example absorbent article.

FIG. 2 depicts a cross-sectional exploded magnified view along 2-2 of the example absorbent article of FIG. 1.

FIG. 3 depicts a top plane view of an example three-dimensional film.

DETAILED DESCRIPTION

Figure 4:
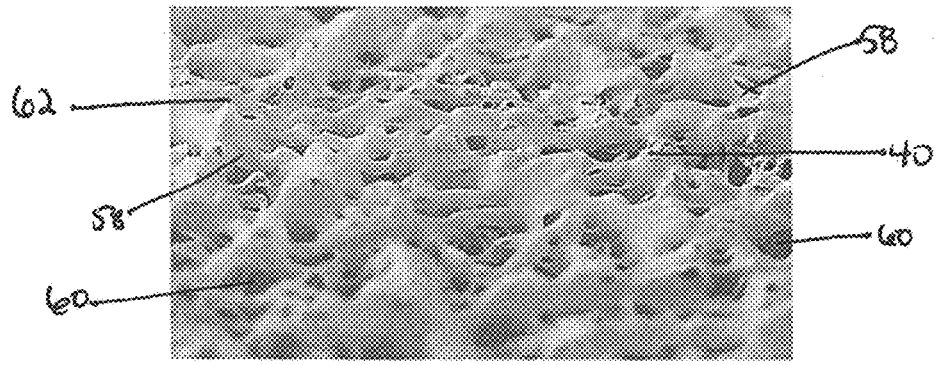
FIG. 4 depicts a perspective magnified top plane view of the example three-dimensional film.
Figure 5:
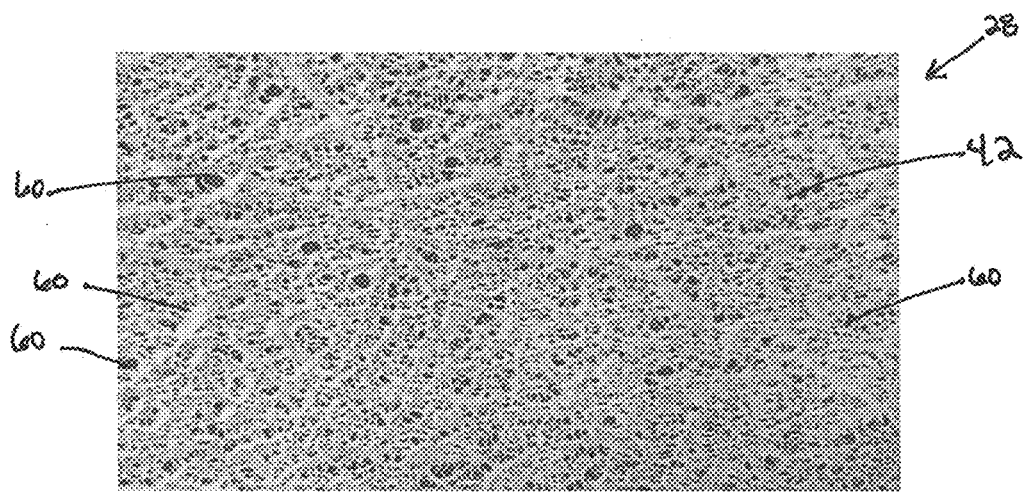
FIG. 5 depicts a bottom plane view of the example three-dimensional film.

A detailed description of illustrative embodiments will now be described with reference to the various Figures. Although this description provides a detailed example of possible implementations, it should be noted that the details are intended to be exemplary and in no way limit the scope of the application.

Examples herein provide a three-dimensional film that may be used as a transfer layer in an absorbent article. The example three-dimensional film may provide a hybrid approach in providing user comfort and performance in handling insults in an absorbent article. The hybrid approach may include a loft structure. The loft structure may be an open lattice structure formed from a single film. In an example, irregular shaped apertures may be present within the loft of the three-dimensional film structure, for example, rather than being present in upper and lower planes of the film.

According to one or more examples, placement of irregularly shaped apertures within the loft of the three-dimensional film may provide for a more nonwoven like structure from a single film structure compared to the current films where apertures originate and terminate in the upper and lower planes of the resilient plastic web.

An absorbent article as described herein may include wearable devices that may absorb and/or hold liquid, and more specifically in examples, may include devices that may be placed against or in proximity to the body of the wearer to absorb and hold various exudates discharged from the body like urine, feces, menstrual fluid, and/or the like. According to an example, the absorbent article may be a disposable absorbent article. A disposable absorbent article includes an absorbent article that may not be intended to be laundered or otherwise restored or reused after use.

FIG. 1 illustrates an example absorbent article 10 that may include the three dimensional film (in one or more examples. As shown in FIG. 1, the absorbent article 10 may be a disposable diaper, adult incontinence implement or article, and/or the like. The absorbent article may generally have a width 12 and a length 14, sometimes also referred to as a lateral axis and longitudinal axis, respectively. The length 14 (longitudinal axis) of the article 10 may be the dimension or direction running from a front edge 20 of the article 10, through a crotch area, to a back edge 16 of the article 10. The width 12 (lateral axis) of the article 10 may be the dimension or direction perpendicular to the longitudinal axis and may run from, for example, a widest point of a first or left edge 22 of the article 10 to, for example, a widest point of a second or right edge 24 of the article 10. Herein, the longitudinal axis or length 14 of the article 10 may be designated as the "Y" direction, the lateral axis or width 12 as the "X" direction as illustrated. In absorbent articles that are worn between the legs such as the article 10, the X-direction may be generally smaller than the Y-direction, for example, particularly in the crotch area.

The absorbent article 10, in an example, may include a fluid collection portion 18 and a backsheet 32 (e.g. as shown in FIG. 2). The fluid collection portion 18 to collect and/or absorb fluid as described herein. For example, the absorbent article 10 may be constructed to have a topsheet material, a three dimensional film, an absorbent core and a backsheet, orientated in that order in a Z-direction. In an example, at least the topsheet, three dimensional film, and absorbent core may be part of the fluid collection portion 18.

FIG. 2 illustrates an example of the absorbent article 10 of FIG. 1 along the line 2-2 illustrating a cross-sectional view thereof (e.g., including a cross-sectional view of the fluid collection portion 18 thereof). As shown and described herein, the absorbent article 10 (e.g., including the fluid collection portion 18) may be constructed to have a topsheet 26, a three-dimensional film 28, an absorbent core 30, and/or a backsheet 32, orientated in that order in a Z-direction. In examples, surfaces and/or planes of the topsheet 26, three-dimensional film, the topsheet 26 (e.g., topsheet material), absorbent core 30, and/or backsheet 32 may be in contact with other respective surfaces or planes as shown. For example, the topsheet 26 may have a first surface 34 and a second surface 36. The first surface 34 may be in contact with skin of a user of the absorbent article 10 and the second surface 36 may be in contiguous contact with a top plane 40 of the three-dimensional film 28. The three-dimensional film 28 may further have a bottom plane 42 that may be in continuous contact with a first surface 46 of the absorbent core 30. As shown, a second surface 48 of the absborbent core 30 may be in contiguous contact with a first surface 52 of the backsheet 32. In an example, a second surface 54 of the back sheet 32 may be the exposed portion (e.g., during use) of the article 10 and/or the outer layer thereof. Further, in an example, the second surface 36 of the topsheet 26 and the first surface 52 of the backsheet 32 may encompass the three-dimensional film 28 width and length and the absorbent core 30 width and length.

The absorbent article 10 may further be constructed to have elastic sections to assist in holding the absorbent article in against or in proximity to the body of the wearer such as elastic waistbands, elastic side panels, hook and loop type closures, elastic leg cuffs. For example, the absorbent article 10 may have also leg cuffs and/or barrier cuffs. The absorbent article 10 may also have elastic members used as waistbands, side panels, side tabs and similar structures. The elastic members may be located at the front edge, back edge, right edge or left edge of the absorbent article. For example, the waistbands may be located at the front edge or the back edge. Leg cuffs may be located at the right edge or left edge.

Three-Dimensional Film

As described, examples herein may provide an absorbent article such as the article 10 comprising the three-dimensional film 28 that may provide a balance between user comforts historically provided by a nonwoven material and provides insult handling found in traditional acquisition distribution layers. The three-dimensional film 28 may be constructed from a single film that may be manipulated into a three-dimensional structure by a formation process, such as vacuum formation, hydroformation or a combination thereof. As shown in FIGS. 2-6, the three-dimensional film 28 may include comprises a top plane 40, a thickness 44, a bottom plane 42, a width, a length and/or a loft. The loft of the three-dimensional film 28 may provide an open lattice structure comprising a random series of interconnected film fibers 58 comprising a plurality of upper peaks and a plurality of lower peaks and a plurality of irregularly shaped apertures 60 (e.g., as shown in FIGS. 3-6). The height (z-dimension) of the loft may be measured between the plurality of upper peaks and plurality of lower peaks. The upper peaks form an upper plane (x-y plane) (e.g., the top plane 40) that tends to be parallel to a lower plane (e.g., the bottom plane 42) formed from the lower peaks. Located between the upper plane and lower plane may be the open lattice structure with the struts of the lattice being formed from the random series of interconnected film fibers 58. These fibers 58 are typically not bonded, but rather result from the manipulation of the single film to result in an integrally formed three-dimensional structure.

Figure 6:
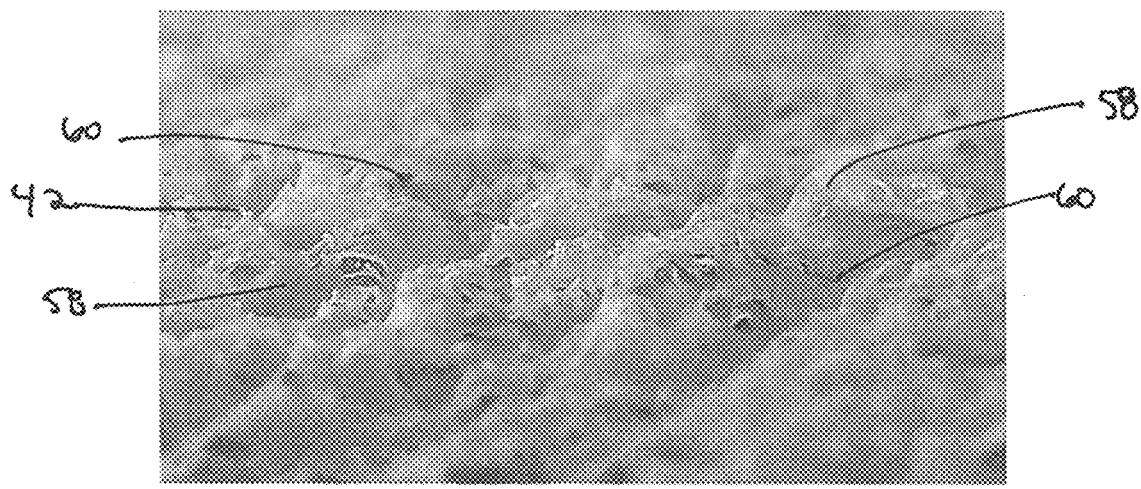
FIG. 6 depicts a perspective magnified bottom plane view of the example three-dimensional film.

In examples, the irregularly shaped apertures 60 of the loft may be defined by the random series of interconnected film fibers 58. The size of the irregularly shaped apertures 60 may be random, but may be between about 3,000 and about 1,250,000 square microns. Given the nature of irregular shapes of the apertures 60, the diameter may not a true diameter, but an effective diameter of about 60 to about 1300 microns. The irregularly shaped apertures 60 may include an orientation predominately orientated in the x-y plane (making them visible from the z-direction), however, the open lattice structure resembles a sponge structure where the irregularly shaped apertures 60 may be orientated at angles (none-orthogonal directions) or perpendicular to the x-y plane randomly throughout the loft of the three-dimensional film 28. The irregularly shaped apertures 60 may be described as having an opening closer to the upper plane 50, a sidewall, and an opening closer to the lower plane 42 as shown. In an example, as shown in FIGS. 4 and 6, an opening closer (e.g., for one of the apertures 60) to the upper plane 40 may be smoother in appearance and an opening closer to the lower plane 42 may be irregular or ragged in appearance of the three-dimensional film 28.

The three-dimensional film 28 may be made from thermoplastic polymeric materials conventionally used to make apertured formed films. For example, the three-dimensional film 28 may comprise one or more of the following: at least one polymer selected from polyolefins (e.g., C2-C10 olefins such as polyethylene, polypropylene, and copolymers); polyesters; plastomers; polyamides (e.g., nylon); polystyrenes; polyurethanes; vinyl polymers; acrylic and/or methacrylic polymers; elastomers (e.g., styrene block copolymer elastomers); polymers from natural renewable sources; biodegradable polymers; and mixtures or blends thereof. According to an example, the thermoplastic material used to make the three dimensional film 28 may include polyethylene having a density in the range of from 0.910 g/cc to 0.960 g/cc, with the more preferred range being from 0.920 g/cc to 0.950 g/cc. The general melt indices range for a typical may be from about 0.10 to about 15 g/10 min., from about 1.5 to about 4.5 g/10 min., and/or the like. The loft of the three-dimensional film 28 may vary from about 400 microns to about 1200 microns, such as about 450 microns to about 1000 microns, such as about 500 microns to 850 microns. Further, in an example, the three-dimensional film 28 may have a basis weight. The basis weight of the three-dimensional film 28 may be defined as the weight of the film per unit area. Basis weight of the film 28 may range from 20-40 gsm. Preferred ranges are from 22-32 gsm, most preferably 22-26 gsm.

Any of a variety of additives may be added to the thermoplastic polymeric materials of the three-dimensional film 28 and may provide certain desired characteristics, including, but not limited to, roughness, reduction of anti-static charge build-up, abrasion resistance, printability, write-ability, opacity, hydrophilicity, hydrophobicity, processability, UV stabilization, color, etc. Such additives are well known in the industry and include, for example, calcium carbonate (abrasion resistance), titanium dioxide (color and opacity), silicon dioxide (roughness), surfactants (hydrophilicity/hydrophobicity), process aids/plastomers (processability), and/or the like. In an example, the three-dimensional film 28 may comprise about 50-60% of high density polyethylene (density of 0.960 g/cc), 20-30% of linear grade low density polyethylene (density of 0.921 g/cc), 4-5% of a white pigment concentrate of inorganic titanium dioxide, and 5-6% of a surfactant concentrate. Other three-dimensional films such as the three-dimensional film 28 may comprise different ratios of high density polyethylene and low density polyethylene.

Topsheet

The topsheet 26 for use in the absorbent article comprises a first surface 34, a second surface 36 and thickness 38 therebetween and may be suitably compliant, soft-feeling and non-irritating to the wearer's skin. The topsheet 26 may be liquid permeable, permitting liquids to readily penetrate through its thickness and may be comprised of a nonwoven or a formed film. The topsheet 26 may be contiguous with the three-dimensional film 28 as described herein (e.g., the second topsheet surface 36 may be contiguous with the top plane 40 of the three-dimensional film) and may extend in the length and width direction beyond the three-dimensional film 28 in the absorbent article, for example, from the front edge and the back edge in the length and to the left edge and the right edge in the width.

In examples herein, the topsheet 26 may include and/or be made of a nonwoven material. Nonwoven materials as used herein may include a manufactured web of directionally or randomly orientated fibers, excluding paper and products which are woven, knitted, tufted, stitch-bonded incorporating binding yarns or filaments, or felted by wet-milling, whether or not additionally needled. Nonwoven materials and processes for making them are known in the art. Generally, processes for making nonwoven materials may comprise laying fibers onto a forming surface, which may comprise spunlaying, meltblowing, carding, airlaying, wet-laying, coform and combinations thereof. The fibers may be of natural or man-made origin and may be staple fibers or continuous filaments or be formed in situ. Any other additional properties of suitable topsheet materials may be provided and/or used in examples herein.

Absorbent Core

The absorbent core 30 may comprise a first surface 46, a second surface 48, a thickness 50 between the first and second surfaces 46,48, a width and a length. The absorbent core's 30 width and the length may be less than the topsheet width and length in an example. Further, the absorbent core's 30 width and length may be greater than the three-dimensional film's 28 width and length. The absorbent core 30 may be orientated in running the length of the absorbent article (e.g., 10) and in the crotch area of the absorbent article. The absorbent core 30 may absorb the insult and may retain the liquid while the absorbent article may be in use. The absorbent core 30 may adequately absorb an insult or multiple insults and substantially retain the insult until the absorbent article may be removed and discarded. The storage capacity of the absorbent core 30 and the efficiency of distribution of an insult across the absorbent core 30 may determine the amount of liquid that may be held in the absorbent article.

The absorbent core 30 that may be used in examples herein may comprise any absorbent material which may be generally compressible, conformable, non-irritating to the wearer's skin, and capable of absorbing and retaining liquids such as urine and other certain body exudates. For example, the absorbent core 30 may include materials such as cellulose materials including fibers, cellular sponge or foam materials, super absorbent materials, such as superabsorbent polymers, hydrocolloidal materials, gel materials and combinations thereof, or any other known absorbent material or combinations of materials. In an example, an absorbent materials that may be used for the absorbent core 30 may include high absorbency gel-type materials that may be generally capable of absorbing about 10 to about 50 times their weight in fluid. As generally described, the rate at which the core absorbs liquids may be inversely proportional to the ability of the core to hold the liquids absorbed. Thus, the superabsorbent materials used in cores (e.g., 30) may be good at holding liquids, but may be relatively slow at liquid uptake. In examples, the delay in liquid uptake results in more unabsorbed or free fluid in the article, and thus decreases the rewet performance of the article.

Backsheet

The backsheet 32 may comprise a first surface 52, a second surface 54, and a thickness 56 between the first and second surfaces 52, 54. In an example, the thickness 56 may be less than 100 microns, such as less than 50 microns. The backsheet 32 may be contiguous with the absorbent core 30 and may extend in the length and width direction beyond the absorbent core 30 in the absorbent article, for example, from the front edge and the back edge in the length and to the left edge and the right edge in the width. The topsheet 26 and backsheet 32 may be continuous (e.g., with each other) at the front edge, back edge, left edge and right edge allowing for the topsheet and backsheet to be bonded together e.g., by gluing or welding by heat or ultrasonic. The backsheet 32 may be a thin (e.g., less than 50 microns in thickness) plastic film, for example, a polyethylene or polypropylene film, a nonwoven material coated with a liquid impervious material, a hydrophobic nonwoven material, which resists liquid penetration or a laminate comprising plastic films and nonwoven materials. The backsheet material may be breathable so as to allow vapor to escape from the absorbent core, while still preventing liquids from passing therethrough.

Breathable backsheets (e.g., that may be used for backsheet 32) may utilize an apertured film or a microporous breathable film, both of which are known in the art, and may also include a nonwoven fibrous web for improved aesthetics and consumer acceptance. Examples of breathable backsheet materials may include porous polymeric films, nonwoven laminates from spunbond and meltblown layers, laminates from porous polymeric films and nonwovens.

Strikethrough

Strikethrough, as utilized herein, is a measure of the time required for a given volume of surfaceapplied liquid to enter, or "strikethrough", a three-dimensional film placed above an absorbent core. In the present series of tests it is a measure of the time in seconds to completely drain 5 milliliters of simulated urine solution having a surface tension of 45 dynes/centimeter from a one inch diameter by ⅝ inch deep cavity having a multiplicity of holes in its lowermost surface. The cavity is integrally formed in a 4 inch by 4 inch strikethrough plate which is placed on a 4 inch by 4 inch sample of the three-dimensional film with filter paper placed underneath to control liquids.

The wearer-contacting surface of the three-dimensional film is oriented top plane facing upwards. An electric timer is started by the simulated urine solution contacting a pair of spaced electrodes in the previously mentioned cavity. The timer automatically shuts off when all of the simulated urine solution has drained from the cavity and into filter paper. Times are reported in seconds. Strikethrough properties less than 1 second are targeted. This may be similar to the strikethrough test described in U.S. Pat. No. 4,601,868.

Rewet

The rewet test comprises wetting a 4 inch by 4 inch sample three-dimensional film while superposed, top plane facing up on top of filter paper with a simulated urine solution having a surface tension of approximately 45 dynes/centimeter until the filter paper has become saturated. A uniform pressure loading of 0.5 p.s.i. is applied to the sample for a period of 3 minutes so that the fluid is uniformly distributed throughout the sample. The pressure is momentarily removed, a pre-weighed second sample of filter paper approximately 15 centimeters in diameter is inserted over the top plane of the three-dimensional film and the predetermined pressure loading is reapplied to the sample for a period of 2 minutes. The second filter paper is then removed and reweighed, and the amount of fluid absorbed by the second filter paper is termed the "rewet" of the sample. Results are expressed in grams of fluid absorbed by the second filter paper. As should thus be apparent, a lower "rewet" number is indicative of a dryer surface feel. Rewet grams less than 1 gram are targeted. This may be similar to the strikethrough test described in U.S. Pat. No. 4,601,868.

Air Permeability

Air permeability of the samples is determined by placing a one inch diameter sample of each three-dimensional film on a Frazier High Pressure Differential Air Permeability Tester, such as is available from Frazier Precision Instrument Company of Gaithersburg, Md. A Frazier No. 8 orifice plate was used. Results were obtained directly from a manometer and converted by means of a standardized chart to provide air flow readings in cubic feet of air per square foot of web material per minute at 30 inches Hg, 70° F., 65% Relative Humidity, the preferable conditions under which the tests are performed.

TABLE 1

Comparison Of Three-Dimensional Film To U.S. Pat. No. 4,601,868

| Test | Non-woven* | U.S. Pat. No. 4,601,868 fiber-like plastic web** | Three-dimensional film | AQP120*** |
|---|---|---|---|---|
| Strikethrough (sec) | 1.57 | 3.45 | 0.71 | |
| Rewet (grams) | 1.66 | 0.03 | 0.046 | |
| Air Permeability Frazier (ft³/ft²/min) | 841 | 677 | 238 | 590 |

*Nonwoven reported in U.S. Pat. No. 4,601,868 in Table 1 (Example 1)
**Reported in U.S. Pat. No. 4,601,868 in Table 1 (Example 3)
***AquiDry Plus™ 120 ex Tredegar Film Products Corporation As shown by Table 1, the performance of the present three-dimensional film demonstrates an improved strikethrough performance than the U.S. Pat. No. 4,601,868 fiber-like plastic web. Air permeability decreases, but the rewet performance remains about the same as the U.S. Pat. No. 4,601,868 fiber-like plastic web, thus demonstrating better fluid handling properties. By comparison, the air permeability of commercially available transfer layer film AquiDry Plus™ is shown.

Sensory Panel Data

A panel of 20 individuals were asked to review absorbent articles with the topsheet in an upwards orientation comprising a series of materials located between the topsheet and the absorbent core for visual softness. Each panelist was asked to rank, based upon visual inspection only, the perceived softness of the center portion of the absorbent article on a scale of 1 to 10, with 10 being the most soft and 1 being the least soft. The test was repeated with two different topsheets, one topsheet being a 17 gsm spunbond nonwoven and the other topsheet being a 22 gsm air through bonded nonwoven. Panelists were not allowed to touch the absorbent articles.

Figure 7:
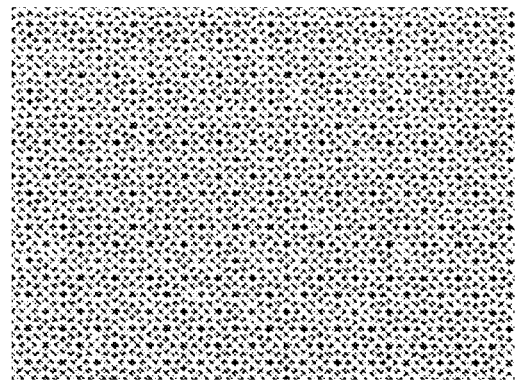
FIG. 7 depicts a view of an example comparative material.
Figure 8:
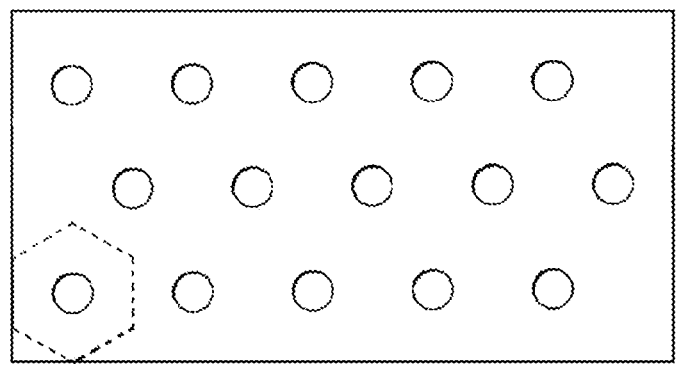
FIG. 8 depicts a view of another example comparative material.
Figure 9:
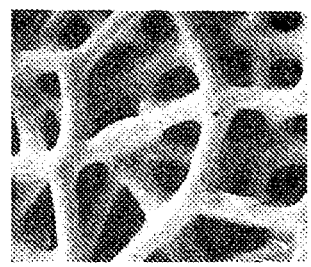
FIG. 9 depicts a portion of the example comparative material illustrated in FIG. 6 of U.S. Pat. No. 4,601,868.
Figure 10:
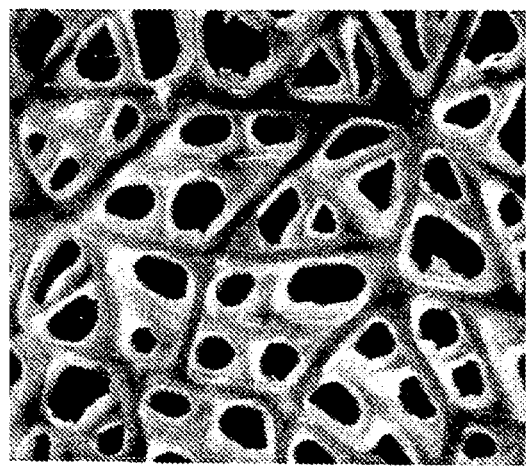
FIG. 10 depicts the example comparative material illustrated in FIG. 7 of U.S. Pat. No. 4,601,868.

The series of materials located between the topsheet included: a nonwoven material; a vacuum formed polyolefin film having an array of 11.2 micron openings in a hexagonal pattern; AQP120—AquiDry Plus™ 120 sold by Tredegar Film Products Corporation; Radel 1 & Radel 2 which is a vacuum formed film described in U.S. Pat. No. 4,601,868 and shown therein in FIGS. 6 & 7 and also shown herein in FIG. 9 of the present application; and the three-dimensional film (e.g., 28) described herein.

TABLE 2

17 gsm spunbond nonwoven topsheet

| non-woven | Radel 1 | Radel 2 | 11.2 micron opening in hexagonal pattern | AQP120 | three-dimensional film |
|---|---|---|---|---|---|
| 7.3 | 5.35 | 5.05 | 5.7 | 6.35 | 6.7 |

As shown in Table 2, panelist on average rated the three-dimensional film closer in visual softness to a nonwoven than the comparative examples while combined with a 17 gsm spunbond nonwoven topsheet.

TABLE 3

22 gsm air through bonded nonwoven topsheet

| non-woven | Radel 1 | Radel 2 | 11.2 micron opening in hexagonal pattern | AQP120 | Present three-dimensional film |
|---|---|---|---|---|---|
| 7.2 | 5.4 | 5.7 | 5.55 | 6.95 | 6.6 |

As shown in Table 3, panelist on average rated the three-dimensional film closer in visual softness to a nonwoven than the comparative examples, except for AQP120, while combined with a 22 gsm air through bonded nonwoven topsheet.

The panelist information (e.g., shown herein) demonstrates that the perceived softness of the three-dimensional film can be compared to nonwoven materials and are visually distinct from the film described in U.S. Pat. No. 4,601,868, a reference that discusses irregularly shaped openings in a formed polymeric film.

Although systems, methods, processes, and/or embodiments may be described herein with respect to various materials, techniques, equipment, such systems, methods, processes, and/or embodiments may be applicable to other applications and environments and may include additional materials, equipment and manufacturing techniques, methods, and/or processes in different orders than those disclosed herein.

The dimensions and values disclosed herein are not to be understood as being strictly limited to the exact numerical values recited. Unless otherwise specified, each such dimension is intended to mean both the recited value and a functionally equivalent range surrounding that value. For example, a dimension disclosed as "100 microns" is intended to mean "about 100 microns."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. An absorbent article comprising:
   a topsheet material having a first surface, a second surface and thickness there between;
   a three dimensional film having a top plane, a thickness, a bottom plane, a width, a length and a loft, the loft comprising an open lattice structure comprising a random series of interconnected film fibers comprising a plurality of upper peaks and a plurality of lower peaks and a plurality of irregularly shaped apertures formed from the random series of interconnected film fibers, the interconnected film fibers being formed from the thickness of the film;
   an absorbent core comprising a first surface, a second surface, a thickness between the first and second surfaces, a width and a length; and
   a backsheet comprising a first surface, a second surface and a thickness between the first and second surfaces,
   wherein the topsheet material second surface and the three-dimensional film top plane are in contiguous contact, the three-dimensional film bottom plane and the absorbent core first surface are in contiguous contact, the absorbent core second surface and the backsheet first surface are in contiguous contact, the topsheet material second surface and the backsheet first surface encompass the three-dimensional film width and length and the absorbent core width and length, the top plane is formed from upper peaks of the random series of interconnected film fibers, the bottom plane is formed from the lower peaks of the random series of interconnected film fibers and the three-dimensional film loft and the lower peaks of the random series of interconnected film fibers comprise the irregularly shaped apertures.

2. The absorbent article of claim 1 wherein the three-dimensional film lower peaks of the random series of interconnected film fibers correspond to the irregularly shaped apertures.

3. The absorbent article of claim 1 wherein the three-dimensional film strikethrough properties are less than 1 second.

4. The absorbent article of claim 1 wherein the three-dimensional film rewet is less than 1 gram.

5. The absorbent article of claim 1 wherein the three-dimensional film comprises a polyolefin.

6. The absorbent article of claim 1 wherein the topsheet comprises a nonwoven with a basis weight of 15-25 gsm.

7. The absorbent article of claim 1 wherein the topsheet is selected from a nonwoven spunbond, an air through bonded nonwoven and a spun lace.

8. The absorbent article of claim 5 wherein the polyolefin comprises polyethylene, polypropylene and mixtures thereof.

9. The absorbent article of claim 1 wherein the irregularly shaped apertures have sizes between about 3,000 and 1,250,000 square microns.

10. The absorbent article of claim 1 wherein the irregularly shaped apertures have effective diameters between about 60 and 1300 microns.

11. The absorbent article of claim 1 wherein the loft is between about 400 and 1200 microns.

12. The absorbent article of claim 11 wherein the loft is between about 450 and 1000 microns.

13. The absorbent article of claim 12 wherein the loft is between about 500 and 850 microns.

14. The absorbent article of claim 1 wherein the three dimensional film has a basis weight between about 20-40 gsm.

15. The absorbent article of claim 14 wherein the three dimensional film has a basis weight between about 22-32 gsm.

16. The absorbent article of claim 15 wherein the three dimensional film has a basis weight between about 22-26 gsm.

17. The absorbent article of claim 1 wherein the three dimensional film comprises at least one additive selected from a group comprising calcium carbonate, titanium dioxide, a surfactant and a process aid/plastomer.

18. The absorbent article of claim 17 wherein the three dimensional film comprises 4-5% titanium dioxide.

19. The absorbent article of claim 17 wherein the three dimensional film comprises 5-6% surfactant.

* * * * *